(12) United States Patent
Chou et al.

(10) Patent No.: US 8,193,325 B2
(45) Date of Patent: *Jun. 5, 2012

(54) PROCESSING METHOD FOR NANO-MINIATURIZING CHITOSAN OF MODIFYING PROPERTY

(75) Inventors: Wen-Tung Chou, Changhua County (TW); Ming-Yi Lai, Changhua County (TW); Kun-Shan Huang, Tainan (TW); Wei-Chun Chen, Banciao (TW)

(73) Assignee: Acelon Chemical and Fiber Corporation, Puyan Township, Changhua County (TW)

( * ) Notice: Subject to any disclaimer, the term of this patent is extended or adjusted under 35 U.S.C. 154(b) by 477 days.

This patent is subject to a terminal disclaimer.

(21) Appl. No.: 12/318,550

(22) Filed: Dec. 31, 2008

(65) Prior Publication Data
US 2009/0227784 A1  Sep. 10, 2009

(30) Foreign Application Priority Data

Dec. 31, 2007  (TW) .............................. 96151669 A (51) Int. Cl.
*C08B 37/08* (2006.01)
*C07H 5/06* (2006.01)
(52) U.S. Cl. .................... 536/20; 536/55.1; 536/55.2
(58) Field of Classification Search .................. None
See application file for complete search history.

(56) References Cited

U.S. PATENT DOCUMENTS

| 6,130,321 | A | 10/2000 | Johnson et al. ............ 536/20 |
| 6,638,918 | B2 | 10/2003 | Davison et al. ............ 514/55 |
| 6,740,752 | B2 * | 5/2004 | Struszcyk et al. ........... 536/124 |
| 6,916,465 | B2 | 7/2005 | Panzer et al. ............. 424/65 |
| 7,094,372 | B1 | 8/2006 | Wang et al. ............. 264/45.1 |
| 7,265,090 | B2 * | 9/2007 | Sung et al. ............. 514/1.2 |
| 2004/0247632 | A1 * | 12/2004 | Cattaneo ............. 424/401 |
| 2009/0166916 | A1 * | 7/2009 | Chou et al. ............. 264/207 |

OTHER PUBLICATIONS

Seo et al., "Simultaneous Depolymerization and Decolorization of Chitosan by Ozone Treatment" Journal of Food Science (2007) vol. 72 No. 9, pp. C522-C526.*
Sandri et al., "Nanoparticles based on N-trimethylchitosan: Evaluation of absorption properties using in vitro (Caco-2 cells) and ex vivo (excised rat jejunum) models" European Journal of Pharmaceutics and Biopharmaceutics (2007) vol. 65 pp. 68-77.*
Yuan et al., "Research on Thymopentin Loaded Oral N-Trirnethyl Chitosan Nanoparticles" Arch Pharm Res (2006) vol. 29 No. 9 pp. 795-799.*
Amidi et al., "Preparation and characterization of protein-loaded N-trimethyl chitosan nanoparticles as nasal delivery system" Journal of Controlled Release (2006) vol. 111 pp. 107-116.*
Schatz et al., "Static Light Scattering Studies on Chitosan Solutions: From Macromolecular Chains to Colloidal Dispersions" Langmuir (2003) vol. 19 pp. 9896-9903.*

* cited by examiner

*Primary Examiner* — Eric S Olson
(74) *Attorney, Agent, or Firm* — Bacon & Thomas, PLLC (57) ABSTRACT

The present invention relates a processing method for nano-miniaturizing chitosan of modifying property, which degrades the chitosan of high molecular weight down to the chitosan of middle and low molecular weight, then primarily nano-miniaturizes the interim chitosan by quaternary ammonium salt/synthesis, finally yield the nano-miniaturized chitosan of modified property by sol-gel method to have features in good biocompatibility and bioactivity to be served as additive material in products of cosmetics, medical treatment, hygiene, health care, biomedicine, agriculture, textile, food and so like so that not only the antiseptic, moisture-retentive and deodorizing capabilities can be promoted but also the processing cost can be reduced due to easiness of the mass production.

20 Claims, 4 Drawing Sheets

*Fig. 8*

PROCESSING METHOD FOR NANO-MINIATURIZING CHITOSAN OF MODIFYING PROPERTY

RELATED APPLICATIONS

This application claims benefit of Taiwan Application No. TW 096151669, filed on Dec. 31, 2007, the entire contents of which are incorporated herein by reference.

FIELD OF THE PRESENT INVENTION

The present invention relates to a processing method for the nano-miniaturizing chitosan of modifying property, which produces desired nano-miniaturized chitosan of modified property by integration in control of molecular weight, quaternary ammonium salt/synthesis and sol-gel method with enhanced features in antiseptic, moisture retentive and deodorizing capabilities so as to provide more application scope and possibility for related industry.

BACKGROUND OF THE INVENTION

For antiseptics and biomedical material application, chitosan is a critical constituent. Therefore, in every country, the industry, scholar organization, academic and scientific institute have invested tremendous resources with every effort to develop and produce modified chitosan and derivatives. However, due to the limitation of antiseptic capability against the microbe and lack activity of fibroblasts for generic chitosan, the practical application from research is confined in the promotion of antiseptic capability and wound dressings (blood coagulation, healing effect and antiseptic capability). Recently, in every country, considerable resources are invested into the research and development in technology of nano-miniaturization. Accordingly, certain momentum for the research and development in nano-miniaturizing chitosan is kindled in most scholar organizations, academic and scientific institutes. Therefore, the business in association with the chitosan will have sound technological basis and potential in the near future.

Other than the foregoing confinement of the chitosan application in the cosmetics, medical treatment and hygiene due to the limitation of antiseptic capability against the microbe and lack activity of fibroblasts for generic chitosan, neither the application of the chitosan in the textile industry nor in the biomedical product is effectively developed. Addressing these facts and issues, the applicant of the present invention contrives the innovative processing method for the nano-miniaturizing chitosan of modifying property.

SUMMARY OF THE INVENTION

The primary object of the present invention is to provide a processing method for nano-miniaturizing chitosan of modifying property, which applies control of molecular weight, quaternary ammonium salt/synthesis and nano-miniaturization to the chitosan to obtain the modified chitosan of degraded and nano-miniaturized with quaternary ammonium salt/synthesis having enhanced capability in antiseptic, moisture-retentive and deodorizing effects so that not only the processing cost can be decreased but also the easiness of mass production can be achieved.

The another object of the present invention is to provide a processing method for nano-miniaturizing chitosan of modifying property, which integrates the processing techniques of control of molecular weight, quaternary ammonium salt/synthesis and nano-miniaturization to the chitosan to yield the nano-miniaturized chitosan of modified property for being blended to develop antiseptic wound dressing and novel textile as well as cosmetological products such as fiber, non-woven, medical dressing, dress, fabric, cosmetic skin mask and the like, wherein the molecular weight of said nano-miniaturized chitosan is less than 50 k.

The other object of the present invention is to provide a processing method for nano-miniaturizing chitosan of modifying property, for producing nano-miniaturized chitosan of modified property for being further introduced into the fiber manufacturing process with Dry-jet Wet Spinning method to manufacture desired fiber fabric having features of enhanced antiseptic, moisture-retentive and deodorizing capabilities.

DETAILED DESCRIPTION OF THE PREFERRED EMBODIMENTS

The processing method for nano-miniaturizing chitosan of modifying property for the present invention comprises processing steps as below.

(a). Degrade the chitosan of high molecular weight into chitosan of middle or low molecular weight for enhancing the antiseptic capability by the procedure of dissolving the chitosan in the diluted acid solution under controlled specific temperature for different reacting time so as to obtain various chitosan of middle or low molecular weight. The exemplary procedure is depicted in the Embodiment [1].

Embodiment [1]

Firstly dissolve the chitosan of high molecular weight (Mw=573200) in the diluted hydrochloric acid (HCl) under controlled reacting temperature of 70° C. for different reacting time of 0.5 hour, 1 hour, 2 hour and 4 hour for degrading the chitosan so that various chitosan of middle or low molecular weight are yielded as listed in the Table (A) below.

TABLE A

| Time (hour) | 0.5 | 1 | 2 | 4 |
|---|---|---|---|---|
| Molecular Weight (Mw) | 173300 | 63600 | 40900 | 20300 |

Listed numerical value above are the Molecular Weight (Mw) for each sample chitosan after different processing time respectively (b). Modify the property of the yielded chitosan in middle or low molecular weight from the foregoing procedure by technique of quaternary ammonium salt/synthesis as primary miniaturizing property modification for water soluble conversion and increasing the antiseptic capability against the bacteria such as acne bacillus by the procedure of dissolving the chitosan in the well-mixed aqueous solution blending with methanol and introduction of iodomethane ($CH_3I$) and sodium chloride (NaCl) so as to separate desired chitosan by acetone for subsequent decompressed drying. The exemplary procedure is depicted in the Embodiment [2].

Embodiment [2]

Firstly dissolve the mixture of chitosan with iodomethane in mole ratio of 1:10 into the aqueous solution of methanol in volume ratio of 11:8 for agitating and mixing diffusion as primary solution; next dissolve the newly-formed mixture primary solution by introducing sodium chloride (NaCl); then separate the collected precipitation by acetone; finally finish the property modification via decompressed drying. Thereby, the functional group of the amine radical on the chitosan is modified into the functional group of the quaternary ammonium salt with resulting property modification rate is approximately 31.2% as shown in the Table (B) below.

TABLE B

| | Elemental analysis | | | |
|---|---|---|---|---|
| Formula | C% | H% | N% | O% |
| $(C_6H_{11}NO_4)_n(161)_n$ | 39.72 | 6.31 | 6.94 | 40.01 |
| $(C_9H_{18}NO_4^+Cl^-)_n(239.5)_n^*$ | 44.87 | 7.11 | 7.55 | 34.5 |

Listed numerical values above are the atomic percentage for each element of C, H, N and O respectively Wherein, the calculating formula for the Ratio of Percentage of Modification Rate by the (iodomethane, $CH_3I$) for (C %) and (H %) is formulated by each following equation respectively.

$$\frac{\left(\frac{72+36x}{204}\right)}{y} = \frac{C\%}{z};\quad \text{formula (1)}$$

$$\frac{\left(\frac{11+7x}{204}\right)}{y} = \frac{H\%}{z};\quad \text{formula (2)}$$

Where, (x) is the Modification Rate Percentage by the (iodomethane, $CH_3I$);
(y) is the total atomic percentage sum for the actual C, H, N and O atoms;
(z) is the total atomic percentage sum for the tabulated C, H, N and O atoms;
(204) is the molecular weight of the ($C_9H_{18}NO_4^+$);
(C %) is the atomic percentage for the tabulated C atoms;
(H %) is the atomic percentage for the tabulated H atoms;

(c). Finally, produce the nano-miniaturized chitosan of modified property by sol-gel method in three following ways respectively: First process, by means of sol-gel method, dissolve the interim chitosan, which is middle and low molecular weight obtained by the previous control of the molecular weight, in the diluted acid solution together with adequate quantity of alkali so that the resulting nano-miniaturized chitosan of colloidal gel structure is produced via hydrolysis, condensation and polymerization with average particle diameter between 82 nm~82.5 nm. The exemplary procedure is depicted in the Embodiment [3] of following paragraph. Second process, by means of sol-gel method too, dissolve the interim chitosan, which is high molecular weight obtained by the previous quaternary ammonium salt/synthesis, in the aqueous solution of de-ionized water together with adequate quantity of alkali so that the resulting nano-miniaturized chitosan of colloidal gel structure is produced via hydrolysis, condensation and polymerization with average particle diameter of 75.5 nm. The exemplary procedure is depicted in the Embodiment [4] of following paragraph. Third process, by means of sol-gel method too, dissolve the interim chitosan, which is middle and low molecular weight obtained by the previous control of the molecular weight and quaternary ammonium salt/synthesis, in the aqueous solution of de-ionized water together with adequate quantity of alkali so that the resulting nano-miniaturized chitosan of colloidal gel structure is produced via hydrolysis, condensation and polymerization with average particle diameter between 65.5 nm~75.5 nm. The exemplary procedure is depicted in the Embodiment [5] of following paragraph.

For the nano-miniaturized chitosan of modified property produced by the above processing steps, each resulting numerical value of the Rate of Water/moisture Absorption (Aw), Rate of Ammonia Absorption (Aa), Bacteriostatic Value (Bs) and the Bactericidal value (Bd) becomes bigger than each initial numerical value of itself. Thus, the capability of respective water/moisture absorption, ammonia absorption, bacteriostasis and the bactericidal ability is considerably increased to have more moisture-retentive, antiseptic and deodorizing capability.

For facilitating you to have further understanding the features of the present invention, we present each experimental embodiment with comparative description in detail as below.

Embodiment [1]

The embodiment relates to the process of chitosan by control of molecular weight.

Degrade the chitosan by dissolving it in the diluted acid under specific reacting temperature for different reacting time so that various chitosan of different molecular weight are yielded. The related Table (C) is attached below for reference.

TABLE C

| Time (hour) | 0.5 | 1 | 2 | 4 |
|---|---|---|---|---|
| Molecular Weight (Mw) | 173300 | 63600 | 40900 | 20300 |

(1): Listed numerical value above are the Molecular Weight (Mw) for each sample chitosan after different processing time respectively.
(2): Original chitosan of high molecular weight, Mw = 573200

Embodiment [2]

The embodiment relates to the process for chitosan of high molecular weight by quaternary ammonium salt/synthesis.

Dissolve the chitosan in the well-mixed aqueous solution blending with methanol and introduction of iodomethane ($CH_3I$) and sodium chloride (NaCl) so as to separate desired chitosan by acetone for subsequent decompressed drying finally. The related Table (D) is attached below for reference.

TABLE D

| Formula | Elemental analysis | | | |
|---|---|---|---|---|
| | C% | H% | N% | O% |
| $(C_6H_{11}NO_4)_n(161)_n$ | 39.72 | 6.31 | 6.94 | 40.01 |
| $(C_9H_{18}NO_4{}^+Cl^-)_n(239.5)_n{}^*$ | 44.87 | 7.11 | 7.55 | 34.5 |

(1): This is the quaternary ammonium salt by the iodomethane ($CH_3I$).
(2): The modification rate of the chitosan is 31.2%.

Embodiment [3]

The embodiment relates to the nano-miniaturizing process for chitosan of middle and low molecular weight by control of molecular weight.

By means of sol-gel method, dissolve the interim chitosan, which is middle and low molecular weight obtained by the previous control of the molecular weight, in the diluted acid solution together with adequate quantity of alkali so that the resulting nano-miniaturized chitosan of colloidal gel structure is produced via hydrolysis, condensation and polymerization.

Figure 1:
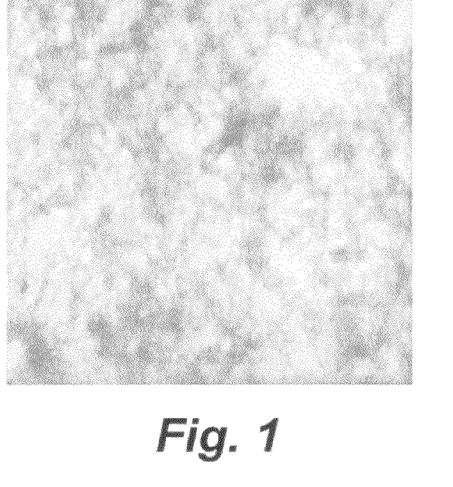
FIG. 1 is a TEM photograph (magnification×20 k) for nano-miniaturized chitosan of low molecular weight (24800) with average particle diameter of 82.0 nm.
Figure 2:
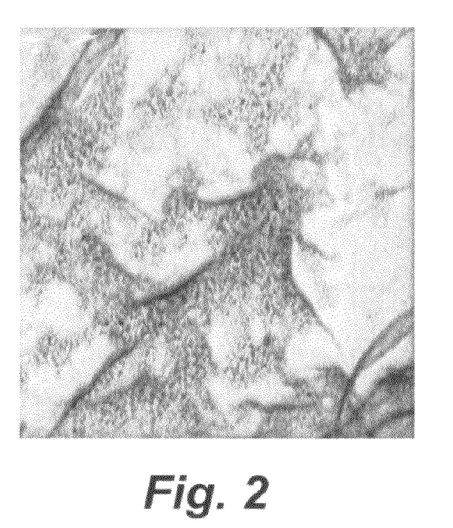
FIG. 2 is a TEM photograph (magnification×20 k) for nano-miniaturized chitosan of middle molecular weight (155895) with average particle diameter of 82.5 nm.

(a). Nano-miniaturization of average particle diameter between 82 nm~82.5 nm (as shown in FIGS. 1 and 2).
(b). Rate of Moisture/Water Absorption:

| Rate of Moisture/Water Absorption | | | |
|---|---|---|---|
| Mw | $W_M$ | $W_D$ | Aw % |
| 24800 | 1.154 g | 0.042 g | 2648 |
| 155895 | 1.668 g | 0.064 g | 2506 |

Mw = molecular weight
$W_M$ = weight of the sample chitosan after absorbing moisture
$W_D$ = weight of the sample chitosan before absorbing moisture
Aw % = percentage rate of moisture/Water absorption Calculating Formula:
The percentage of the Moisture/Water Absorption Rate (Aw %) is calculated by following formula.

$$\text{Moisture/Water Absorption Rate: } Aw\% = \{[W_M(g) - W_D(g)]/W_D(g)\} \times 100$$

Where, WM (g) is the weight of the sample chitosan after absorbing moisture in gram unit.
WD (g) is the weight of the sample chitosan before absorbing moisture in gram unit.

(c). deodorization

The experiment for evaluating deodorizing effect is on the testing basis in absorption of the ammonia odor. Testing method is that first fill the ammonia gas of specific concentration into the air-tight bottle; next put the sample modified chitosan of the present invention of specific quantity into the same bottle aforesaid for 15 minutes absorption; then measure the gas concentration in the sample chitosan before and after putting into the bottle by gas chromatograph.

The ratio of the deodorizing property for ammonia absorption rate (Aa) is calculated by following formula.

$$\text{Deodorization(Test of Ammonia Absorption Rate)} Aa = (C_O - C_A)/C_O$$

Where, $C_O$ is the original gas concentration in the sample chitosan before absorbing ammonia.
$C_A$ is the absorbed gas concentration in the sample chitosan after absorbing ammonia for 15 minutes.

| Deodorization: Test of Ammonia Absorption | | | |
|---|---|---|---|
| Mw | $C_O$ | $C_A$ | Aa |
| 24800 | 890 ppm | 350 ppm | 540 ppm |
| 155895 | 970 ppm | 420 ppm | 550 ppm |

Mw = molecular weight
$C_O$ = original gas concentration in the sample chitosan before absorbing ammonia
$C_A$ = absorbed gas concentration in the sample chitosan after absorbing ammonia for 15 minutes
Aa = rate of ammonia absorption
Aa % = percentage rate of ammonia absorption
The (Aa %) for chitosan (Mw = 24800) is (60.7%).
The (Aa %) for chitosan (Mw = 155895) is (56.7%).

Embodiment [4]

The embodiment relates to the nano-miniaturizing process for chitosan of high molecular weight by quaternary ammonium salt.

By means of sol-gel method, dissolve the interim chitosan, which is high molecular weight obtained by the previous quaternary ammonium salt/synthesis, in the aqueous solution of deionization water together with adequate quantity of alkali so that the resulting nano-miniaturized chitosan of colloidal gel structure is produced via hydrolysis, condensation and polymerization.

Figure 3:
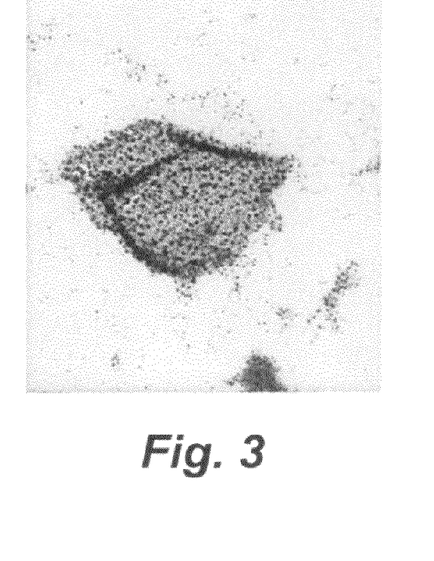
FIG. 3 is a TEM photograph (magnification×20 k) of nano-miniaturizing process for chitosan of high molecular weight (573200) by quaternary ammonium salt with average particle diameter of 75.5 nm.
Figure 4:
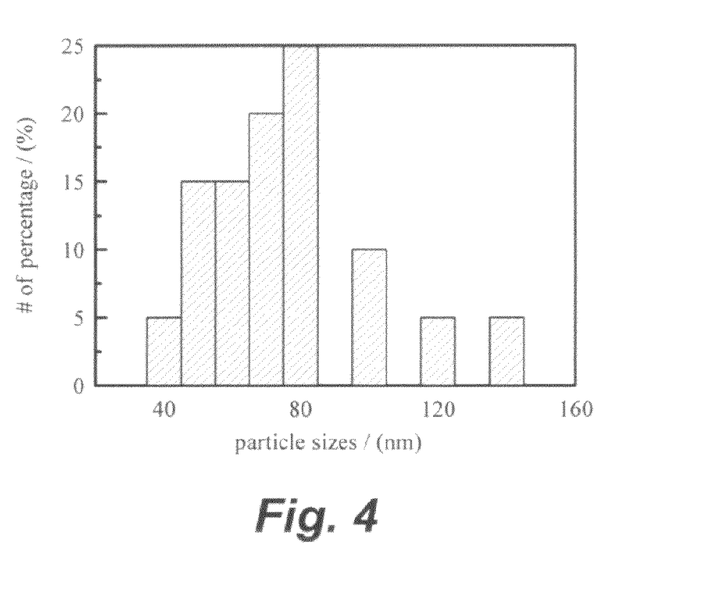
FIG. 4 is a distribution illustration of nano-miniaturizing process for chitosan of high molecular weight (573200) by quaternary ammonium salt with average particle diameter of 75.5 nm.

(a). Nano-miniaturization of average particle diameter is 75.5 nm (as shown in FIGS. 3 and 4).
(b). Rate of Moisture Absorption=3059% ($5.732 \times 10^5$ g/mole)

| Rate of Moisture/Water Absorption | | | |
|---|---|---|---|
| Mw | $W_M$ | $W_D$ | Aw % |
| 573200 | 2.559 g | 0.081 g | 3059 |

Mw = molecular weight
$W_M$ = weight of the sample chitosan after absorbing moisture
$W_D$ = weight of the sample chitosan before absorbing moisture
Aw % = percentage rate of Moisture/Water absorption Calculating Formula:
The percentage of the Moisture/Water Absorption Rate (Aw %) is calculated by following formula.

$$\text{Moisture/Water Absorption Rate: } Aw\% = \{[W_M(g) - W_D(g)]/W_D(g)\} \times 100$$

Where, WM (g) is the weight of the sample chitosan after absorbing moisture in gram unit.
WD (g) is the weight of the sample chitosan before absorbing moisture in gram unit.

(c). deodorization=62.5% ($5.732 \times 10^5$ g/mole)

The experiment for assaying deodorizing effect is on the testing basis in absorption of the ammonia odor. Testing method is that first fill the ammonia gas of specific concentration into the air-tight bottle; next put the sample modified chitosan of the present invention of specific quantity into the same bottle aforesaid for 15 minutes absorption; then measure the gas concentration in the sample chitosan before and after putting into the bottle by gas chromatograph.

The ratio of the deodorizing property for ammonia absorption rate (Aa) is calculated by following formula.

Deodorization(Test of Ammonia Absorption Rate)$Aa=(C_O-C_A)/C_O$

Where, $C_O$ is the original gas concentration in the sample chitosan before absorbing ammonia.

$C_A$ is the absorbed gas concentration in the sample chitosan after absorbing ammonia for 15 minutes.

| Deodorization (Test of Ammonia Absorption) | | | |
|---|---|---|---|
| Mw | $C_O$ | $C_A$ | Aa |
| 573200 | 960 ppm | 360 ppm | 600 ppm |

Mw = molecular weight
$C_O$ = original gas concentration in the sample chitosan before absorbing ammonia
$C_A$ = absorbed gas concentration in the sample chitosan after absorbing ammonia for 15 minutes
Aa = rate of ammonia absorption
Aa % = percentage rate of ammonia absorption
The (Aa %) for chitosan (Mw = 573200) is (62.5%).

Embodiment [5]

The embodiment relates to the nano-miniaturizing process for chitosan of middle and low molecular weight by control of molecular weight and quaternary ammonium salt.

By means of sol-gel method, dissolve the interim chitosan, which is middle and low molecular weight obtained by the previous control of molecular weight and quaternary ammonium salt/synthesis, in the aqueous solution of deionization water together with adequate quantity of alkali so that the resulting nano-miniaturized chitosan of colloidal gel structure is produced via hydrolysis, condensation and polymerization.

Figure 5:
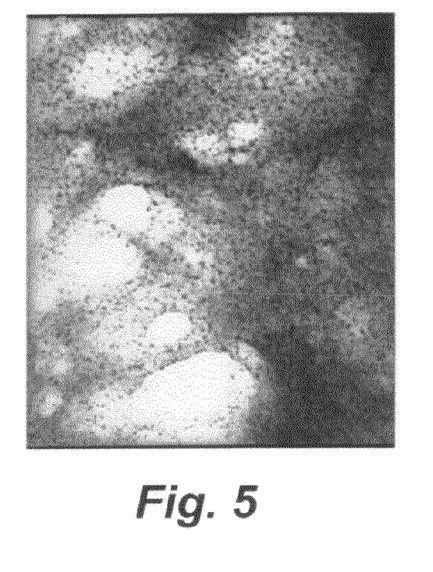
FIG. 5 is a TEM photograph (magnification×20 k) of nano-miniaturizing process for chitosan of low molecular weight (24800) by quaternary ammonium salt with average particle diameter of 65.5 nm.
Figure 6:
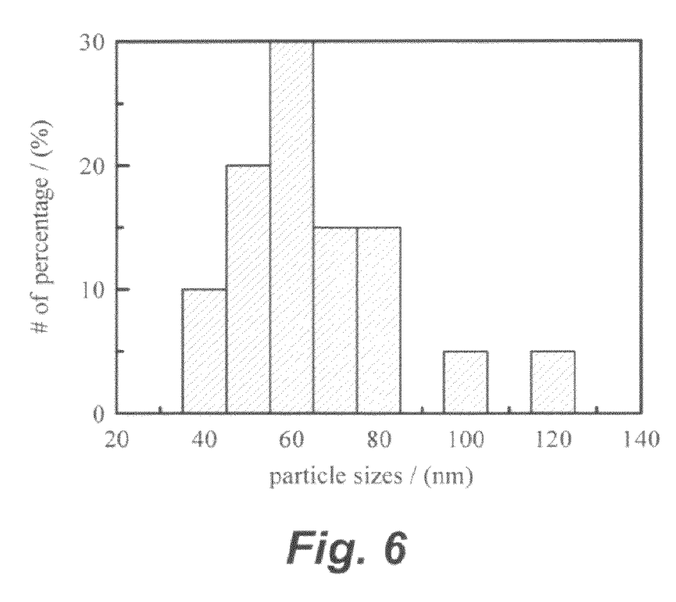
FIG. 6 is a distribution illustration of nano-miniaturizing process for chitosan of low molecular weight (24800) by quaternary ammonium salt with average particle diameter of 65.5 nm.
Figure 7:
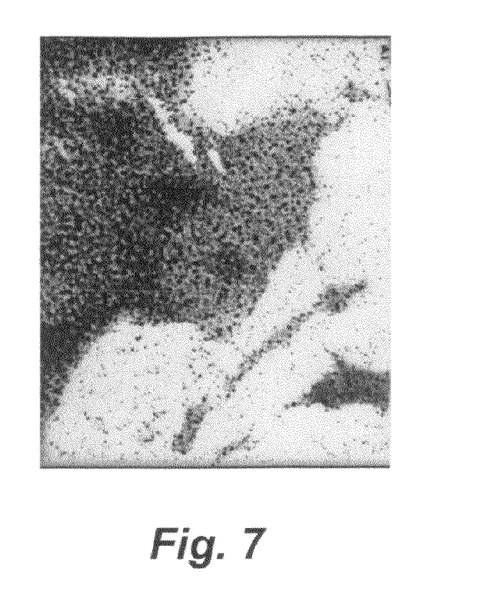
FIG. 7 is a TEM photograph (magnification×20 k) of nano-miniaturizing process for chitosan of middle molecular weight (155895) by quaternary ammonium salt with average particle diameter of 75.5 nm.
Figure 8:
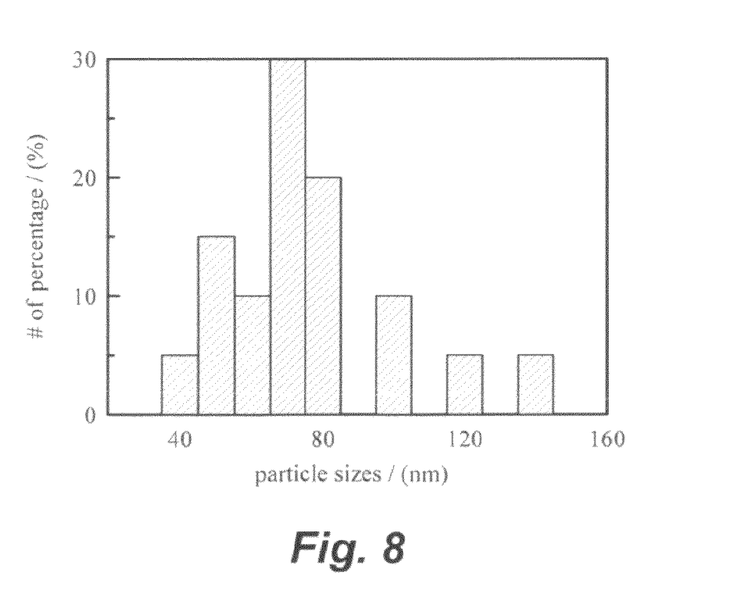
FIG. 8 is a distribution illustration of nano-miniaturizing process for chitosan of middle molecular weight (155895) by quaternary ammonium salt with average particle diameter of 75.5 nm.

(a). Nano-miniaturization of average particle diameter for low molecular weight (24800) is 65.5 nm (as shown in FIGS. 5 and 6). Nano-miniaturization of average particle diameter for middle molecular weight (155895) is 75.5 nm (as shown in FIGS. 7 and 8).

(b). Rate of Moisture/Water Absorption

| Rate of Moisture/Water Absorption | | | |
|---|---|---|---|
| Mw | $W_M$ | $W_D$ | Aw % |
| 24800 | 2.584 g | 0.075 g | 3345 |
| 155895 | 2.893 g | 0.089 g | 3151 |

Mw = molecular weight
$W_M$ = weight of the sample chitosan after absorbing moisture
$W_D$ = weight of the sample chitosan before absorbing moisture
Aw % = percentage rate of moisture/water absorption Calculating Formula:

The percentage of the Moisture/Water Absorption Rate (Aw %) is calculated by following formula.

The percentage of the Moisture/Water Absorption Rate (Aw %) is calculated by following formula.

Moisture/Water Absorption Rate: $Aw\% = \{[W_M(g) - W_D(g)] / W_D(g)\} \times 100$ Where, $W_M$ (g) is the weight of the sample chitosan after absorbing moisture in gram unit.

$W_D$(g) is the weight of the sample chitosan before absorbing moisture in gram unit.

(c). deodorization

The experiment for assaying deodorizing effect is on the testing basis in absorption of the ammonia odor. Testing method is that first fill the ammonia gas of specific concentration into the air-tight bottle; next put the sample modified chitosan of the present invention of specific quantity into the same bottle aforesaid for 15 minutes absorption; then measure the gas concentration in the sample chitosan before and after putting into the bottle by gas chromatograph.

The ratio of the deodorizing property for ammonia absorption rate (Aa) is calculated by following formula.

Deodorization(Test of Ammonia Absorption Rate)$Aa=(C_O-C_A)/C_O$

Where, $C_O$ is the original gas concentration in the sample chitosan before absorbing ammonia.

$C_A$ is the absorbed gas concentration in the sample chitosan after absorbing ammonia for 15 minutes.

| Deodorization (Test of Ammonia Absorption) | | | |
|---|---|---|---|
| Mw | $C_O$ | $C_A$ | Aa |
| 24800 | 900 ppm | 300 ppm | 600 ppm |
| 155895 | 970 ppm | 340 ppm | 630 ppm |

Mw = molecular weight
$C_O$ = original gas concentration in the sample chitosan before absorbing ammonia
$C_A$ = absorbed gas concentration in the sample chitosan after absorbing ammonia for 15 minutes
Aa = rate of ammonia absorption
Aa % = percentage rate of ammonia absorption
The (Aa %) for chitosan (Mw = 24800) is (66.7%).
The (Aa %) for chitosan (Mw = 155895) is (64.95%).

Embodiment [6]

The embodiment relates to the comparative experiment of antiseptic capability for the nano-miniaturized chitosan of modified property with testing result being tabulated as below.

The experiment is performed in accordance with (JIS L1902-1998 Quantitative Method).

Testing Bacteria:

Type (A) of testing bacteria is Methicillin Resistant Staphyloccous Aureus (MRSA) (ATCC 6538P); and Type (B) of testing bacteria is Klebsiella Pheumoniae (ATCC 4352).

Calculating Formula:

The growing activity value of the bacteria (BGA) is calculated by following formula and the incubated bacteria concentration within $1.0 \pm E^{+5}$ (number/ml) means valid for the experiment.

Growing Activity value of the Bacteria: $BGA = \log(Mb) - \log(Ma)$

Bacteriostatic value of the sample: $Bs = \log(Mb) - \log(Mc)$

Bactericidal value of the sample: $Bd = \log(Ma) - \log(Mc)$

Where,

Ma is bacteria number of un-processed sample in immediate count upon cleansing without incubation.

Mb is bacteria number of un-processed sample after being incubated for 18~24 hours.

Mc is bacteria number of processed sample after being incubated for 18~24 hours.

Bs is Bacteriostatic value of the sample.

Bd is Bactericidal value of the sample.

Assaying Criterion:

According to norm from the "Japan Association of Fiber Evaluating Technology for new function" (JAFET), the antiseptic criterion is that:

The experiment is valid if the incubated bacteria concentration ($C_{IB}$) within $1.0 \pm E^{+5}$ (number/ml).

The experiment is valid if the Growing Activity value of the Bacteria BGA>1.5.

The testing sample has bacteriostatic effect if its bacteriostatic value Bs>2.2.

The testing sample has bactericidal effect if its bactericidal value Bd>0.

Where, the numerical ($1.3E^{+4}$) denotes 13,000 with analog so forth.

| MRSA | Fabric$_{WC}$ | NM M-Mw | NM L-Mw | NM4⁰A H-Mw |
|---|---|---|---|---|
| $C_{IB}$ | $1.2E^{+5}$ | $1.2E^{+5}$ | $1.2E^{+5}$ | $1.2E^{+5}$ |
| Ma | $2.3E^{+4}$ | — | — | — |
| Mb | $2.0E^{+7}$ | — | — | — |
| Mc | — | <20 | <20 | <20 |
| BGA | 2.9 | — | — | — |
| Bs | — | 6.0 | 6.0 | 6.0 |
| Bd | — | 3.1 | 3.1 | 3.1 |

(MRSA) = Methicillin Resistant *Staphyloccous Aureus* (MRSA)
(KsPm) = *Klebsiella Pheumoniae*
(Fabric$_{wc}$) = white cotton fabric
(NM) = nano-miniaturized sample
(NM4⁰A) = nano-miniaturized quaternary ammonium salt
(H-Mw) = high molecular weight
(M-Mw) = middle molecular weight
(L-Mw) = low molecular weight
($C_{IB}$) = incubated bacteria concentration
(Ma) = bacteria number of un-processed sample in immediate count upon cleansing without incubation
(Mb) = bacteria number of un-processed sample after being incubated for 18~24 hours
(Mc) = bacteria number of processed sample after being incubated for 18~24 hours
(BGA) = Growing Activity value of the Bacteria
(Bs) = Bacteriostatic value of the sample
(Bd) = Bactericidal value of the sample

| MRSA | Fabric$_{WC}$ | NM4⁰A M-Mw | NM4⁰A L-Mw |
|---|---|---|---|
| $C_{IB}$ | $1.2E^{+5}$ | $1.2E^{+5}$ | $1.2E^{+5}$ |
| Ma | $2.3E^{+4}$ | — | — |
| Mb | $2.0E^{+7}$ | — | — |
| Mc | — | <20 | <20 |
| BGA | 2.9 | — | — |
| Bs | — | 6.0 | 5.6 |
| Bd | — | 3.1 | 2.9 |

| KsPm | Fabric$_{WC}$ | NM M-Mw | SN L-Mw | NM4⁰A H-Mw |
|---|---|---|---|---|
| $C_{IB}$ | $1.2E^{+5}$ | $1.2E^{+5}$ | $1.2E^{+5}$ | $1.2E^{+5}$ |
| Ma | $2.3E^{+4}$ | — | — | — |
| Mb | $3.2E^{+7}$ | — | — | — |
| Mc | — | <20 | <20 | <20 |
| BGA | 3.1 | — | — | — |
| Bs | — | 6.2 | 6.2 | 6.2 |
| Bd | — | 3.1 | 3.1 | 3.1 |

(MRSA) = Methicillin Resistant *Staphyloccous Aureus* (MRSA)
(KsPm) = *Klebsiella Pheumoniae*
(Fabric$_{wc}$) = white cotton fabric
(NM) = nano-miniaturized sample
(NM4⁰A) = nano-miniaturized quaternary ammonium salt
(H-Mw) = high molecular weight
(M-Mw) = middle molecular weight
(L-Mw) = low molecular weight
($C_{IB}$) = incubated bacteria concentration
(Ma) = bacteria number of un-processed sample in immediate count upon cleansing without incubation
(Mb) = bacteria number of un-processed sample after being incubated for 18~24 hours
(Mc) = bacteria number of processed sample after being incubated for 18~24 hours
(BGA) = Growing Activity value of the Bacteria
(Bs) = Bacteriostatic value of the sample
(Bd) = Bactericidal value of the sample

| KsPm | Fabric$_{WC}$ | NM4⁰A M-Mw | NM4⁰A L-Mw |
|---|---|---|---|
| $C_{IB}$ | $1.2E^{+5}$ | $1.2E^{+5}$ | $1.2E^{+5}$ |
| Ma | $2.3E^{+4}$ | — | — |
| Mb | $3.2E^{+7}$ | — | — |
| Mc | — | <20 | <20 |
| BGA | 3.1 | — | — |
| Bs | — | 6.2 | 6.1 |
| Bd | — | 3.1 | 2.9 |

In conclusion, the antiseptic, moisture-retentive and deodorizing effects for the nano-miniaturized and property-modified chitosan, which has been sequentially processed by degrade of molecular weight, quaternary ammonium salt/synthesis and nano-miniaturization in the present invention, can be further effectively enhanced so that not only the antiseptic, moisture-retentive and deodorizing capabilities can be promoted but also the processing cost can be reduced due to easiness of the mass production when the modified chitosan is introduced into the products of cosmetics, medical treatment, hygiene, health care, biomedicine, agriculture, textile, food and so on. Thus, it really has innovative novelty beyond obviousness of the prior arts and practical industrial usage, which meet the basic criterion of the patentability. Accordingly, we submit the patent application in accordance with the related patent law.

What is claimed is:

1. A method for producing nano-miniaturized chitosan of colloidal gel structure, comprising:
    (a)(i) reducing the molecular weight of chitosan by dissolving chitosan of a high molecular weight in a diluted acid solution under controlled specific temperature for different reacting times so as to obtain chitosan having a molecular weight between 10 and 50 kD, and/or (ii) modifying (A) chitosan of high molecular weight or (B) chitosan of molecular weight between 10 and 50 kD of step (a)(i) by dissolving the chitosan in a well-mixed solution of water and methanol, introducing iodomethane ($CH_3I$) and sodium chloride (NaCl) to the solution, separating the chitosan by acetone precipitation, drying the chitosan using decompressed drying, and dissolving the chitosan in an aqueous solution of de-ionized water, so as to obtain chitosan wherein the amine radical functional group of the chitosan is modified into a quaternary ammonium salt functional group; and (b) nano-miniaturizing the chitosan of step (a) by a sol-gel method comprising adding an adequate quantity of alkali to the chitosan of step (a), and hydrolyzing, condensing, and polymerizing the chitosan, so as to produce a nano-miniaturized chitosan of colloidal gel structure, wherein the particle diameter for said nano-miniaturized chitosan of colloidal gel structure is approximately between 40 and 150 nm.

2. The method of claim 1, wherein a preserving agent is further added to said aqueous solution of de-ionized water of step (a)(ii).

3. The method of claim 1, wherein said diluted acid solution of step (a)(i) comprises acetic acid, lactic acid or acrylic acid.

4. The method of claim 1, wherein the concentration of acid in said diluted acid solution of step (a)(i) is between 0.5 and 5.0%.

5. The method of claim 1, wherein said alkali of step (b) is sodium hydroxide (NaOH) or ammonia water.

6. The method of claim 1, wherein the concentration of said alkali of step (b) is between 0.5 and 5.0%.

7. The method of claim 1, wherein the molecular weight for said chitosan of high molecular weight is over 200 kd.

8. The method of claim 1, wherein said controlled specific temperature of step (a)(i) is 70° C.

9. The method of claim 1, wherein in step a(i) the chitosan of a high molecular weight is dissolved in the diluted acid solution for 0.5, 1, 2, or 4 hours.

10. The method of claim 1, wherein the particle diameter for said nano-miniaturized chitosan of colloidal gel structure is approximately between 65.5 and 82.5 nm.

11. The method of claim 1, wherein said method comprises step (a)(ii).

12. A method for producing nano-miniaturized chitosan of colloidal gel structure, comprising:
(a)(i) optionally reducing the molecular weight of chitosan by dissolving chitosan of a high molecular weight in a diluted acid solution under controlled specific temperature so as to obtain various chitosan of middle or low molecular weight, and (ii) modifying (A) chitosan of high molecular weight or (B) chitosan of middle or low molecular weight of step (a)(i) by dissolving the chitosan in a well-mixed solution of water and methanol, introducing iodomethane ($CH_3I$) and sodium chloride (NaCl) to the solution, separating the chitosan by acetone precipitation, drying the chitosan using decompressed drying, and dissolving the chitosan in an aqueous solution of de-ionized water, so as to obtain chitosan wherein the amine radical functional group of the chitosan is modified into a quaternary ammonium salt functional group; and (b) nano-miniaturizing the chitosan of step (a) by a sol-gel method comprising adding an adequate quantity of alkali to the chitosan of step (a), and hydrolyzing, condensing, and polymerizing the chitosan, so as to produce a nano-miniaturized chitosan of colloidal gel structure.

13. The method of claim 12, wherein the particle diameter for said nano-miniaturized chitosan of colloidal gel structure is approximately between 40 and 150 nm.

14. The method of claim 12, wherein the molecular weight for said chitosan of middle molecular weight is between 100 and 200 kd.

15. The method of claim 12 wherein the molecular weight for said chitosan of low molecular weight is between 10 and 50 kd.

16. The method of claim 12, wherein the molecular weight for said chitosan of high molecular weight is over 200 kd.

17. A method for producing nano-miniaturized chitosan of colloidal gel structure, comprising:
(a)(i) reducing the molecular weight of chitosan by dissolving chitosan of a high molecular weight in a diluted acid solution under controlled specific temperature so as to obtain various chitosan of molecular weight between 10 and 50 kD or (ii) obtaining various chitosan of molecular weight between 10 and 50 kD;

(b) optionally modifying the chitosan of step (a) by dissolving the chitosan in a well-mixed solution of water and methanol, introducing iodomethane ($CH_3I$) and sodium chloride (NaCl) to the solution, separating the chitosan by acetone precipitation, drying the chitosan using decompressed drying, and dissolving the chitosan in an aqueous solution of de-ionized water, so as to obtain chitosan wherein the amine radical functional group of the chitosan is modified into a quaternary ammonium salt functional group; and (c) nano-miniaturizing the chitosan of step (a) or step (b) by a sol-gel method comprising adding an adequate quantity of alkali to the chitosan of step (a) or step (b), and hydrolyzing, condensing, and polymerizing the chitosan, so as to produce a nano-miniaturized chitosan of colloidal gel structure.

18. The method of claim 17, wherein the particle diameter for said nano-miniaturized chitosan of colloidal gel structure is approximately between 40 and 150 nm.

19. The method of claim 17, wherein said method comprises step (a)(ii).

20. The method of claim 17, wherein the molecular weight for said chitosan of high molecular weight is over 200 kd.

* * * * *